US00PP37383P2

(12) United States Plant Patent
Li

(10) Patent No.: US PP37,383 P2
(45) Date of Patent: Apr. 28, 2026

(54) ***PORTULACA* PLANT NAMED 'NUFPO24119'**

(50) Latin Name: *Portulaca oleracea*
Varietal Denomination: NUFPO24119

(71) Applicant: KLEMM + SOHN GMBH & CO. KG, Stuttgart (DE)

(72) Inventor: Ruijun Li, North Parramatta (AU)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/235,100

(22) Filed: Jun. 11, 2025

(51) Int. Cl.
*A01H 5/02* (2018.01)
*A01H 6/00* (2018.01)

(52) U.S. Cl.
USPC ..... Plt./471

(58) Field of Classification Search
USPC ..... Plt./471
CPC ..... A01H 5/02; A01H 5/00; A01H 6/00
See application file for complete search history.

(56) References Cited

U.S. PATENT DOCUMENTS

PP30,415 P2 * 4/2019 Li ..... A01H 5/02
Plt./471

* cited by examiner

*Primary Examiner* — June Hwu
(74) *Attorney, Agent, or Firm* — Weatherly IP Solutions, LLC; James M. Weatherly

(57) ABSTRACT

A new *Portulaca* plant designated 'NUFPO24119' particularly distinguished by large flowers with a magenta star pattern and a yellow background; and compact and spreading plant habit, is disclosed.

1 Drawing Sheet

Genus and species: *Portulaca oleracea.*
Variety denomination: 'NUFPO24119'.

BACKGROUND OF THE NEW PLANT

The present invention comprises a new and distinct variety of *Portulaca*, botanically known as *Portulaca oleracea*. and hereinafter referred to by the variety name 'NUFPO24119'. 'NUFPO24119' originated from a controlled cross in December 2020 at Cobbitty, Australia between the proprietary female *Portulaca* variety 'PO21.15.10' (unpatented) and the proprietary male *Portulaca* parent 'PO21.15.18' (unpatented).

Seeds from the controlled cross were obtained. The seeds were sown and plants were grown for evaluation. A single plant was selected in October 2021 and subsequently named 'NUFPO24119'. In December 2021 'NUFPO24119' was first vegetatively propagated by vegetative stem cuttings in Cobbitty, Australia. 'NUFPO24119' was found to reproduce true to type in successive generations of asexual propagation via stem cuttings in Cobbitty, Australia.

SUMMARY

The following are the most outstanding and distinguishing characteristics of 'NUFPO24119' when grown under normal horticultural practices in Cobbitty, Australia:

1. Large flowers with a magenta star with a yellow background; and
2. Compact and spreading plant habit.

DESCRIPTION OF THE PHOTOGRAPH

This new *Portulaca* plant is illustrated by the accompanying photograph of a 14-week-old plant grown outdoors in Stuttgart, Germany during August 2024. The colors shown are as true as can be reasonably obtained by conventional photographic procedures. The photograph is a whole plant photo of 'NUFPO24119' and shows the foliage, buds, and flowers.

DESCRIPTION

The following detailed descriptions set forth the distinctive characteristics of 'NUFPO24119'. The data which define these characteristics were collected from asexual reproductions carried out in Cobbitty, Australia from 3-month-old plants in 2022. Color references are to The R.H.S. Colour Chart of The Royal Horticultural Society of London (R.H.S.), 5$^{th}$ edition (2007).

Classification:
- *Family.*—Portulacaceae.
- *Botanical.—Portulaca oleracea.*
- *Designation.*—'NUFPO24119'.
- *Type.*—Purslane.

Parentage:
- *Female parent.*—'PO21.15.10' (unpatented).
- *Male parent.*—'PO21.15.18' (unpatented).

Plant description:
- *Habit and form.*—Compact and spreading.
- *Height.*—3.3 cm.
- *Spread.*—27.0 cm.
- *Time and conditions to produce a rooted cutting.*—5 to 8 days.
- *Life cycle.*—Annual.
- *Flowering requirements.*—Spring to Autumn.

Stems:
- *General description.*—Round with slight ridges.
- *Stem color.*—RHS 145A.
- *Anthocyanin.*—Absent.

*Pubescence*.—Absent.
*Diameter*.—0.26 cm.
*Length*.—14.0 cm to 20.0 cm.
*Internode length*.—2.2 cm.
*Branching*.—Moderate.

Leaves:
*Arrangement*.—Alternate, simple.
*Shape*.—Obovate.
*Apex*.—Acute, becoming more rounded with development.
*Base*.—Attenuate.
*Margin*.—Entire.
*Leaf attachment*.—Petiolate.
*Leaf length*.—1.8 cm.
*Leaf width*.—1.1 cm.
*Leaf thickness*.—0.15 cm.
*Texture*.—Upper surface: Smooth, glabrous, succulent. Lower surface: Smooth, glabrous, succulent.
*Leaf color*.—Upper surface: RHS 137B with very narrow reddish margin, RHS 59B. Lower surface: RHS 138B.
*Leaf surface pubescence*.—Absent.
*Venation*.—Pinnate.
*Petiole*.—Length: 0.2 cm. Diameter: 0.15 cm. Color: RHS 145B.
*Fragrance*.—None detected.

Inflorescence:
*Type*.—Solitary, sessile.
*Flowering habit*.—Freely flowering habit and most flowers face upright.
*Time to bloom from propagation*.—Approximately 8 weeks.
*Lastingness of individual blooms on the plant*.—1 to 2 days.
*Flower diameter*.—3.9 cm.
*Flower depth*.—1.4 cm.
*Fragrance*.—None detected.

Flower bud:
*Surface appearance and texture*.—Shiny, pubescent.
*Shape*.—Ovoid.
*Bud length*.—0.7 cm.
*Bud diameter*.—0.5 cm.
*Bud color*.—RHS 144A.

Corolla:
*Shape*.—Obovate, single flower with five slightly overlapping petals.
*Petal number per flower*.—5 petals.
*Petal pubescence*.—Smooth, glabrous.
*Petal size*.—Length: 1.9 cm. Width: 1.3 cm.
*Petal apex*.—Emarginate.
*Petal margin*.—Entire.
*Petal color*.—Upper surface: RHS 67B magenta stars from narrow at the petal base to widening towards the petal apex with RHS 12D yellow background, RHS 58B rings occurring at the base of the petals. Lower surface: RHS 67C magenta stars from narrow at the petal base to widening towards the petal apex with RHS 12D yellow background.
*Intensity of petal overlap*.—Slight or weak.
*Depth of the emarginated petal apex*.—Shallow.

Calyx:
*Arrangement*.—Two and base fused.
*Sepals*.—Shape: Deltoid. Apex: Acute. Margin: Entire. Length: 0.7 cm. Diameter: 0.5 cm. Color: RHS 146D. Texture: Upper surface: Smooth. Lower surface: Smooth. Appearance: Double lobed.

Reproductive organs:
*Stamens*.—Number per flower: About 50 to 56 per flower. Form: Free. Length: 0.6 cm. Pollen amount: Abundant. Pollen color: RHS 23A.
*Fragrance*.—Absent.
*Placental arrangement*.—Central. Pistil number per flower: 1. Pistil length: 1.3 cm. Stigma color: RHS 145D. Stigma length: 0.3 cm. Style length: 1.1 cm. Style color: RHS 145D.

Seeds:
*Production*.—About 10 seeds per flower.
*Diameter*.—1.0 mm.
*Color*.—RHS 200B.

Disease and insect resistance: No particular disease or insect resistance observed.

COMPARISON WITH PARENTAL AND COMMERCIAL VARIETIES

'NUFPO24119' is distinguished from the parents as described in Table 1.

TABLE 1

Comparison with Parental Varieties

| Characteristic | 'NUFPO24119' | Female parent 'PO21.15.10' | Male Parent 'PO21.15.18' |
|---|---|---|---|
| Bicolor pattern | Magenta star with yellow background | Magenta Star with white background | Magenta Star with yellow background |
| Flower size | Bigger than 'PO21.15.10' but smaller than 'PO21.15.18' | Smaller than 'NUFPO24119' | Bigger than 'NUFPO24119' |

'NUFPO24119' can be compared to the commercial *Portulaca* variety 'KLEPO17022' (U.S. Plant Pat. No. 30,415). Differences between the varieties are described in Table 2.

TABLE 2

Comparison with Similar Commercial Variety

| Characteristic | 'NUFPO24119' | 'KLEPO17022' |
|---|---|---|
| Bicolour pattern | Magenta star with yellow background | Magenta Star with white background |
| Earliness | Earlier than 'KLEPO17022' | Later than 'NUFPO24119' |

I claim:

1. A new and distinct cultivar of *Portulaca* plant named 'NUFPO24119' as illustrated and described herein.

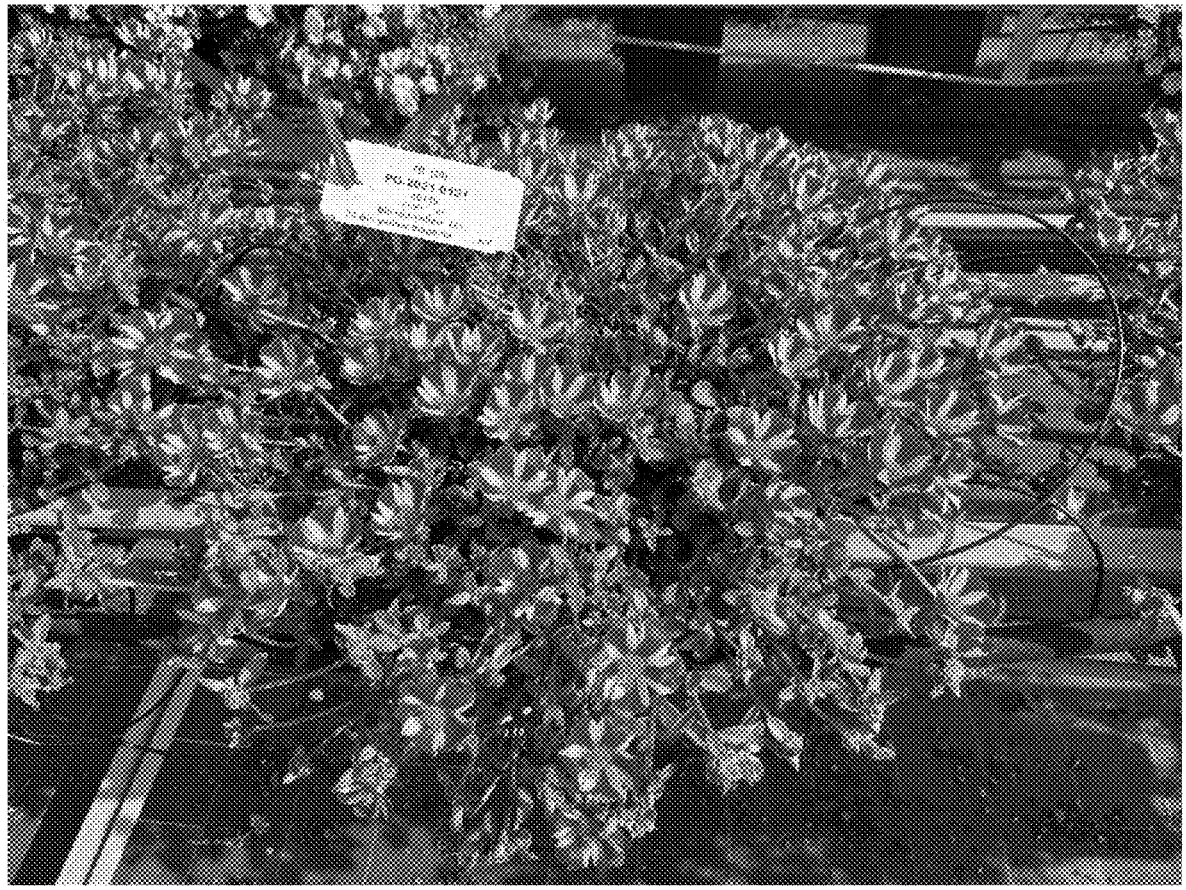

* * * * *